United States Patent [19]
Perricone

[11] Patent Number: 6,051,244
[45] Date of Patent: Apr. 18, 2000

[54] FRUCTOSE DIPHOSPHATE TOPICAL COMPOSITIONS

[76] Inventor: Nicholas V. Perricone, 27 Coginchaug Ct., Guilford, Conn. 06437

[21] Appl. No.: 09/134,600

[22] Filed: Aug. 14, 1998

Related U.S. Application Data

[63] Continuation-in-part of application No. 08/009,840, Jan. 27, 1993, abandoned.

[51] Int. Cl.[7] .............................. A61K 9/00; A61K 47/26
[52] U.S. Cl. ........................... 424/401; 514/23; 514/886; 514/887; 514/912; 514/914; 514/937; 514/944; 514/969
[58] Field of Search ..................................... 424/401, 456, 424/417, 420; 514/23, 828, 858–865, 870, 871, 886, 887, 938, 944, 969, 912, 914; 536/17.1, 117

[56] References Cited

U.S. PATENT DOCUMENTS

| | | | |
|---|---|---|---|
| 4,448,711 | 5/1984 | Catlani | 424/180 |
| 4,873,223 | 10/1989 | Vinas | 514/23 |

*Primary Examiner*—Gollamudi S. Kishore
*Attorney, Agent, or Firm*—St. Onge Steward Johnston & Reens LLC

[57] ABSTRACT

Topical application of fructose-1,6-diphosphate, its derivatives and/or precursors are used for treating or preventing epidermal or mucosal aging and inflammation. In preferred embodiments, the fructose diphosphate (or its derivative) is applied in admixture with a dermally, ophthalmically, orally, or nasally acceptable carrier. Topical application lessens symptoms of urticaria, atopic dermatitis and allergic rhinitis and conjunctivitis among other inflammatory conditions and inhibit microscarring of the dermis.

5 Claims, No Drawings

FRUCTOSE DIPHOSPHATE TOPICAL COMPOSITIONS

RELATED APPLICATION DATA

This application is a continuation-in-part of copending U.S. application Ser. No. 08/009,840, filed Jan. 27, 1993 now abandoned.

TECHNICAL FIELD OF THE INVENTION

The present invention relates primarily to the topical application of fructose diphosphate, or its derivatives, for the treatment of acute and chronic conditions of the skin and mucosa. Therapies according to the invention reduce or prevent tissue degenerative effects of aging and inflammatory disease using, as an active ingredient, a compound that participates widely in normal metabolic pathways.

BACKGROUND OF THE INVENTION

Epidermal inflammation and aging are closely related phenomena. So similar are the processes involved with both, that aging is sometimes described dermatologically as a chronic low grade inflammatory condition. In acute inflammation, there can be a respiratory burst of neutrophil activity that initiates cascades that typically involve a change in the oxidation state of the cell. Acute inflammation is also characterized by mast cell degranulation wherein serotonin is produced, which acts as a signal transduction factor. Following that, excited oxygen species are generated, e.g., superoxide anion, and these damage the lipid-rich membranes and activate the chemical mediators of proinflammation and inflammation. Alteration in the redox state of the cell activates transcription factors such as NFκB as well as AP1, which then causes production of proinflammation mediators. These mediators, such as TFα and various interleukins, cause a burst of cytokines. Arachadonic acid is released, which is oxidized to biologically active mediators. When arachadonic acid is oxidized via the cyclooxygenase or lipoxygenase pathways, for example, prostaglandins, leukotrines, and hyroxyeicosatetraenoic acid (HETE) are produced, which cause erythma, edema, and free radical production. Transcription factors such as NFκB and AD1 alter DNA expression in the cell and produce cytokines and proteinases such as collagenase.

Similar metabolic events are observed in epidermal aging. Cell age is due in part to free radical damage, which takes place mostly within the cell membrane. The cell membrane is most susceptible to attack by free radicals because of its dense molecular structure largely comprising lipids and lipoproteins, which are easily oxidized by reactive oxygen species. In the epidermis, reactive oxygen species such as singlet oxygen, the superoxide anion, and hydroxyl radicals, as well as other free radicals, are generated in normal metabolism, as well as through ultraviolet sun exposure, other forms of radiation, other environmental factors such as pollution or exposure to chemicals in the home or workplace, and the like, active in the arachidonic acid cascade. As in inflammation, free radicals activate chemical mediators that produce prostaglandins and/or leukotrines.

The body contains an endogenous antioxidant defense system made up of antioxidants such as vitamins C and E, glutathione, and enzymes, e.g., superoxide dismutase. When metabolism increases or the body is subjected to other stress such as infection, extreme exercise, radiation, or chemicals, the endogenous antioxidant systems are overwhelmed, and free radical damage takes place. Over the years, the cell membrane continually receives damage from reactive oxygen species and other free radicals, resulting in cross-linkage or cleavage or proteins and lipoprotins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

In aging, the regularity of tissue structure is lost. Individual cells enlarge, but the total number of cells decreases approximately 30%. The dermis microscars and diminishes with loss of elastic and collagen fibers. Cross-linking between longchain collagen macromolecules occurs. Elastin loses its discrete structure.

As mentioned above, at least some mast cell degranulation is observed in most acute pathological inflammatory processes. Upon being activated by any of a number of stimuli, mast cells degranulate, expelling secretory granule contents and releasing pharmacologic mediators. The consequences of mediator release may be apparent within minutes or may require hours to develop. Among the mast cell-derived mediators, either preformed within the granules or generated from precursor molecules, are kinins and kininogen, thromboxanes, leukotrienes $C_4$, $D_4$ and $E_4$, easinophil chemotactic factors of anaphylaxis, heparin, superoxide dismutase mutase, prostaglandins, platelet-activating factor, neutrophil chemotactic factor of anaphylaxis, inflammatory factors of anaphylaxis, and a number of enzymes including proteinases such as chymotrypsin, trypsin, and collagenase. Serotonin is produced, which acts as a signal transduction factor.

Mast cell degranulation is observed in a number of pathological processes and conditions of the skin and mucosa. These include urticaria (hives), allergic conjunctivitis (an inflammatory disease of eye mucous membranes), allergic rhinitis (an inflammatory disease of nasal mucous membranes), atopic dermatitis, cutaneous mastocytosis (an abnormal increase in mast cells), and various allergic and immune complex-mediated inflammations. In all these, degranulation either causes or exacerbates symtoms of the malady, which even in mild cases include elevated, erythematous, pruritic wheals or serpiginous exanthem, usually surrounded by areas of erythema in hives; nasal stuffiness, paroxysms of sneezing, profuse mucous secretion and frequent itching of the nose and posterior pharynx in allergic rhinitis; and soreness or inflammation of the conjunctivae, with excessive tearing and mucoid conjunctival discharge and frequent itching of the eyes, in allergic conjunctivitis. Periodontal disease is an inflammatory disorder of the gums variously referred to as gum disease, periodontitis, and gingivitis; the disorder typically results from the accumulation of plaque, particularly within the gum line, which, unless effectively removed, produces a chronic inflammatory process of the gingiva that spreads and destroys the connective tissues supporting the tooth as well as the tooth itself. It is not uncommon for patients to exhibit fatigue, malaise, anorexia and irritability as a result of their uncomfortable pathological skin or mucosal conditions, and pronounced and chronic cases exhibit worse symptoms and can develop serious complications which are sometimes life-threatening.

A number of treatments have been suggested for symtomatic relief of these disorders. These include antihistamines and other decongestants, topical corticosteroids, systemic steroids, and, in the case of periodontal disease, a vigorous and sustained program of brushing and flossing. All have limitations and/or side effects. Uriticarias, for example, can be caused by a variety of agents including drugs, foods, food additives, inhaled and contact allergens, exposure to sun, heat, and cold, exercise, and different immune complex-induced and complement-related disorders, and so treatment of choice can vary a great deal among the different types depending upon the underlying diagnosis. Anti-inflammatory agents useful for some uriticarias may exacerbate others. Effective removal of plaque is difficult in many cases of periodontal disease.

As summarized by Frost in U.S. Pat. No. 5,057,322, in a disclosure directed to the treatment of extreme mast cell disease such as urticaria pigmentosa and systemic mastocytosis, conventional therapy for mast cell disease is typically palliative and symtomatic, and includes transfusions, antimicrobials, antihistamines, adrenal steroids, corticotropin, roentgen irradiation, and nitrogen mustard (column 1, line 67 to column 2, line 2). Frost remarked that "[t]here does not currently exist any modality of drug treatment for mast cell disease" (column 2, lines 38 to 39), and suggested using an opioid antagonist such as naltrexone or nalmefene (id., lines 50 to 52).

Antihistamines have been suggested for the treatment of pruritic conditions such as contact dermatitis, allergic dermatitis, urticaria, insect bites, mast cell disease and reactions to intradermal allergy testing (U.S. Pat. No. 5,098,717 to Blackman, column 1, line 66, to column 2, line 2). Allergic rhinitis is commonly treated with antihistamines, but use of many of these causes sedation and excessive drying. Alpha-adrenergic agonists in nasal sprays and drops may yield initial relief to some patients, but use of these compounds for more than a few days often results in progressively severe nasal obstruction secondary to rebound swelling of the nasal mucosa. A 4% solution of cromolyn sodium (e.g., Nasalcrom™ and Opticrom™) applied topically can also be beneficial in the treatment and prevention of allergic rhinitis and conjunctivitis if administered frequently. The PDR reports that cromolyn sodium inhibits mast cell degranulation which occurs after exposure to specific antigens by blocking calcium ion entry into mast cells, and has the advantage of having no intrinsic bronchodilator or antihistamine activity (*Physicians Desk Reference*, 52$^{nd}$ ed., Medical Economics Company, N.J., 1998, p. 2367). However, the beneficial effects of the nostril spray with this agent may not be noted until 2 to 4 weeks after initiation of the treatment, so there is a need for an antihistamine or decongestant before cromolyn's preventive effect becomes apparent. Ophthalmic solutions can become contaminated.

Topical corticosteroids have been employed in the treatment and prevention of allergic rhinitis, but these may cause local burning, irritation, and occasional epistaxis or mild nasopharyngeal candidiasis in some patients, and the drugs do not relieve ocular symptoms. Systemic steroids administered by a nasal inhaler are sometimes used, but there is substantial evidence that no effects occur in adults who use up to 800 $\mu$g daily (approximately 16 inhalations), and these drugs must be used with caution in the presence of (possibly undiagnosed) viral and fungal nasal diseases in which there appears to be an associated defect in cell-mediated immunity.

It would be useful to have additional topical compositions for the treatment of acute epidermal and mucosal conditions involving inflammation, including those related to mast cell degranulation, especially for urticaria, atopic dermatitis, cutaneous mastocytosis, allergic conjunctivitis, and allergic rhinitis, as well as those observed after surgery or other trauma from accidents and the like. It would also be useful to have therapies directed to chronic conditions which function using the same or analogous biochemical pathways, such as aging, radiation-induced skin damage, and periodontal disease.

SUMMARY OF THE INVENTION

A primary objective of this invention is to provide methods and compositions for treatment and/or prevention of aging and inflammation of the skin and mucosa.

It is a further objective of the invention to provide methods and compositions for the treatment of pathological conditions of the skin or mucosa which involve, at least in part, mast cell degranulation.

It is a more particular objective of the invention to provide for the treatment and/or prevention of aging and various dermatologic conditions as well as allergic conditions of the eyes and respiratory tract based upon topical application to exposed or affected epidermal or mucosal areas of an active agent or precursor or derivative thereof, preferably in association with a dermally, ophthalmically, orally or nasally acceptable carrier or vehicle.

These and other objectives are accomplished by the present invention, which provides a method and composition for the treatment and/or prevention of skin or mucosal aging or inflammation, which comprises topical application to affected sites of an effective amount of fructose-1,6-diphosphate, its derivatives or precursors, or mixtures thereof.

In the preferred practice of the invention, the fructose-1,6-diphosphate (or derivative or precursor) is applied in admixture with a dermally, ophthalmically, orally or nasally acceptable carrier or vehicle (e.g., as a lotion, cream, ointment, drop, spray, wash, or the like) so as to facilitate topical application and, in some cases, provide additional therapeutic effects as might be brought about, e.g., by moisturizing of the affected skin areas or soothing the ocular, oral or nasal mucosa.

The amount of the fructose-1,6-diphosphate or its derivative or precursor or mixtures thereof (hereinafter referred to collectively as fructose-1,6-diphosphate for ease of reference) necessary to bring about anti-aging or anti-inflammatory effects or the therapeutic treatment of the skin or mucosa is not fixed per se, and necessarily is dependent upon the severity and extent of the condition, the nature of the skin or mucosa, the identity and form of fructose-1,6-diphosphate employed, and the concentration of the fructose-1,6-diphosphate when employed in association with a carrier. Generally the fructose-1,6-diphosphate or composition containing it is topically applied to the affected skin, eye, mouth, or nose areas in a predetermined or as-needed regimen to bring about improvement, it generally being the case that gradual improvement is noted with each successive application. Insofar as has been determined based upon clinical studies to date, no adverse side effects are encountered.

DETAILED DESCRIPTION OF THE INVENTION

This invention is based upon the finding that fructose-1,6-diphosphate, a natural substance involved in the glycolytic path in all mammalian tissues, has efficacy in the prevention of aging and inflammation in epidermal and mucosal tissues. The compound and/or its derivatives inhibit microscarring of the dermis. They also inhibit inflammation. Though previously suggested as an inhibitor of histamine release from mast cells in some tissues and useful in the treatment of adult respiratory distress and aleviation pulmonary edema, (U.S. Pat. No. 4,703,040 to Markov), it has now been found that the sugar can be employed in the treatment of epidermal and mucosal conditions involving the generalized degranulation of mast cells in amounts and under conditions unrelated to antihistamine activity, and in the treatment of aging tissue.

The invention describes methods for the treatment and/or prevention of aging and inflammation, including pathological epidermal and mucosal conditions involving mast cell degranulations, such as urticaria, and allergic rhinitis and conjunctivitis, by the topical application of fructose-1,6-diphosphate, fructose-1,6-diphosphate derivatives, fructose-1,6-diphosphate precursors, and mixtures thereof to affected epidermal or mucosal areas.

As used herein, the term "fructose-1,6-diphosphate", also called 1,6-bis(dihydrogen phosphate), 1,6-D-fructosediphosphoric acid, or hexose diphosphate), includes the α-D-metabolite of the glycolytic and photosynthetic pathways which has the following formula:

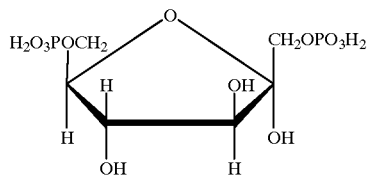

as well as its corresponding isomers and mixtures thereof. Fructose-1,6-diphosphate is commercially available or can be prepared by the action of yeasts on glucose, mannose, fructose or sucrose, or by enzymatic conversion from precursors (e.g., from fructose-6-phosphate by the action of phosphohexokinase or from glucose-6-phosphate by the action of phosphohexose isomerase and phosphohexokinase).

"Derivatives" of fructose-1,6-diphosphate are those which preserve or provide the effective compound upon dissolution or dispersion in a carrier or upon topical application. These include salts, and mixtures thereof with each other and with fructose diphosphate. Many typical emobidments of fructose diphosphate derivatives are salts including, but not limited to, the barium salt, the calcium salt, the potassium salt, the sodium salt, the dibarium salt, the dicalcium salt, the dimagnesium salt, the disodium salt, the trisodium salt, the tetrasodium salt, the tricyclohexylamine salt, the tetrasodium salt, mixed ion salts, and mixtures thereof. The salts may be anhydrous or hydrated. One embodiment employs sodium or potassium salts, including the trisodium salt. As used herein, a "salt" includes compounds having one or more cations complexed with the phosphate groups of fructose diphosphate.

"Precursors" of fructose-1,6-diphosphate also provide the effective compound upon topical application and typically include its metabolic precursors in carbohydrate metabolism such as, for example, glucose-6-phosphate, fructose-6-phosphate or mixtures of these, as well as derivatives of the precursors such as, for example, the corresponding barium, calcium, sodium, potassium, disodium, dipotassium, dicyclohexylamine salts of the phosphorylated sugars. These yield fructose-1,6-diphosphate by enzymic conversion as described above. As used herein, where methods provide an "effective amount" of 1,6-fructose diphosphate to ameliorate symtoms of epidermal or mucosal aging and/or inflammation, the methods include treatment with precursors as well as, or instead of, 1,6-fructose diphosphate and/or its salts or other derivatives.

Fructose-1,6-diphosphate and its derivatives, precursors, and mixtures thereof are generally soluble in water. Since topical application to affected sites of epidermal or mucosal damage according to the invention requires that the active ingredient be in a form permitting such use, it generally will be the case that the diphosphate or precursor or derivative be employed in association with a carrier, and particularly one in which the active ingredient is soluble per se or is effectively solubilized (e.g., as an emulsion or microemulsion). It is necessary that the carrier be inert in the sense of not bringing about a deactivation of the diphosphate or its derivative or precursor, and in the sense of not bringing about any adverse effect on the skin or mucosal areas to which it is applied.

For skin surfaces, suitable carriers include water, alcohols, oils and the like, chosen for their ability to dissolve or disperse the active ingredient at concentrations of active ingredient most suitable for use in the therapeutic treatment. Generally, even low concentrations of active ingredient in a carrier will be suitable, requiring only that more frequent topical application be resorted to. Chronic conditions typically require a lower concentration of active ingredient than to acute conditions. As a practical matter, however, to avoid the need for repeated application, it is desirable that the topically applied composition (i.e., fructose-1,6-diphosphate or precursor or derivative plus carrier) be formulated to contain at least about 1% by weight, more preferably at least about 3 to 10% by weight, with one particularly preferred embodiment containing from about 2% to about 5% by weight, of the active ingredient for the treatment of acute conditions. For the treatment of chronic conditions, the amounts typically vary from about 0.05% or about 0.1% to about 3% to about 5% by weight. Accordingly, carriers will be chosen which can solubilize or disperse the active ingredient at such concentrations. In typical embodiments, these exhibit little or no intrinsic antihistamine activity, i.e., binding to $H_1$ or $H_2$ receptors.

While the carrier for the diphosphate or its derivative or precursor for skin compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many such dermatological compositions are known in the art, and can take the form of lotions, creams, gels, soaps, or even solid compositions (e.g., stick-form preparations). Typical compositions include lotions containing oils and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Indeed, two particularly preferred embodiments are oil-in-water creams and lecithin gels. Such compositions are referred to herein as dermally or dermatologically acceptable carriers.

Carriers for fructose-1,6-diphosphate or its derivative or precursor for eye and nose compositions are generally preferred to comprise those inocuous to these more sensitive mucosal surfaces. Generally, the carrier and active ingredient composition for ocular preparations are physiological solutions or ointments, and those for nasal preparations form a film or layer so as to localize the application and provide some resistance to removal by mucous secretion. Many such compositions are known in the art, and can take the form of salves, jellies, drops or sprays. Drops or sprays are particularly desirable for the compositions of this invention because of the solubility of fructose-1,6-diphosphate in water. Preferred ophthalmic preparations are isotonic and sterile for therapeutic instillation of the solution, and similar preparations can be employed as nasal solutions for administration by inhalation. In some embodiments, the concentration of active ingredient ranges from about 1% to about 5%, preferably about 2% in these aqueous compositions. Typical compositions also include non-toxic buffering salts such as those typically found in physiological saline, such as sodium phosphate salts and potassium and sodium chloride, glycerin, gums and emollients that preserve the mucous membranes while soothing nose and eye itching and inflammation as much as possible. Such compositions are referred to herein as ophthalmically or nasally acceptable carriers. For use in oral therapies, including not only periodontal disease but also for treatments around sensitive and problem teeh, canker and other mouth sores, and after surgery, active ingredient is typically applied in a toothpaste or mouthwash.

In order to demonstrate the efficacy of fructose-1,6-diphosphate in the treatment of dermatologic conditions involving mast cell degranulation, compositions containing about 5% of the trisodium salt of fructose-1,6-diphosphate in an oil-in-water cream and the same concentration of the diphosphate salt in a lecithin gel were prepared. Ten subjects having urticarial lesions (hives) were employed in the study. The fructose diphosphate lecithin gel compositions were applied to half the lesions on each subject 2 to 3 times a day; lecithin gel was applied to the untreated lesions as a control. Resolution of treated lesions was observed in all subjects within 30 minutes, while the untreated lesions remained unchanged for 6 to 8 hours. One subject having a particularly severe case of hives applied the 5% fructose diphosphate composition to all lesions and obtained almost complete remission after a week of treatment.

Five subjects with atopic dermatitis were treated with the 5% fructose diphosphate oil-in-water cream composition in a parallel study. Skin areas treated with the fructose diphosphate preparation exhibited diminished scaling, but not pruritis. All the subjects receiving treatment reported reduction in symptoms of the respective skin conditions in both studies.

An isotonic, sterile solution containing 2% fructose-1,6-diphosphate trisodium salt was employed as an ophthalmic drop and nasal spray to four subjects having allergic rhinitis and conjunctivitis. The treatments were administered as much as wanted for relief. All the subjects reported reduction in symptoms.

In another study, seven patients with cutaneous mastocytosis received two coded creams, one which was a placebo, and another which contained 1,6-fructose diphosphate. Both were applied to separate lesions on each patient twice daily. Two physicians independently observed clearing of some of the leasions at approximately 6 to 8 weeks of use. After breaking the code, it was found that the patients using 1,6-fructose diphosphate were those in which the resolution of lesions was observed.

The method and compositions of the present invention are particularly useful for preventing or treating aging and inflamed tissue, including the treatment of pathological epidermal conditions involving mast cell degranulation such as urticaria, atopic dermatitis and cutaneous mastocytosis, and mucosal conditions involving mast cell degranulation such as allergic rhinitis and conjunctivitis and for wound treatment, including surgical wounds. Moreover, topical application of fructose-1,6-diphosphate or its derivatives or precursors according to the invention can also be effective to prevent symptoms in aging persons for the inhibition of microscarring of the dermis and to promote collagen production, for persons susceptible to periodontal disease, for persons allergic to ragweed, tree pollens, grass pollens, animal danders, and the like prior to exposure to the allergen where this is known or expected to occur. It is an advantage of the invention that treatment or preventive measures employ, as an active ingredient, a natural compound found in normal tissue.

Since mast cell degranulation is observed in other pathological conditions such as anaphylaxis, gastroenteritis and other disorders of the gastrointestinal tract and the likely mechanism of action of fructose-1,6-diphosphate in the inhibition of degranulation, the method of this invention can also be employed systemically in the treatment of these and related conditions. The routes of administration can be oral or intravenous.

All papers, book excerpts, and patents cited herein are hereby fully incorporated by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless otherwise indicated.

What is claimed is:

1. A method for the treatment of skin aging which comprises topically applying to affected skin areas a composition containing an active ingredient selected from the group consisting of fructose 1,6-diphosphate, fructose 1,6-diphosphate salts, and mixtures thereof, in an amount effective to inhibit loss of elastic and collagen fibers in the dermis.

2. A method according to claim 1 wherein the composition further prevents free radical production.

3. A method according to claim 1 wherein the effective amount is one that exhibits no intrinsic antihistamine activity.

4. A method according to claim 1 wherein the active ingredient comprises a fructose-1,6-diphosphate potassium or sodium salt.

5. A method according to claim 1 wherein the composition comprises from about 0.05% to about 5% active ingredient.

* * * * *